(12) United States Patent
Amirparviz et al.

(10) Patent No.: US 8,446,341 B2
(45) Date of Patent: *May 21, 2013

(54) CONTACT LENS WITH INTEGRATED LIGHT-EMITTING COMPONENT

(75) Inventors: Babak Amirparviz, Seattle, WA (US); Tueng T. Shen, Redmond, WA (US); Andrew Lingley, Seattle, WA (US)

(73) Assignee: University of Washington, Seattle, WA (US)

( * ) Notice: Subject to any disclaimer, the term of this patent is extended or adjusted under 35 U.S.C. 154(b) by 836 days.

This patent is subject to a terminal disclaimer.

(21) Appl. No.: 12/463,847

(22) Filed: May 11, 2009

(65) Prior Publication Data

US 2010/0001926 A1 Jan. 7, 2010

Related U.S. Application Data

(63) Continuation-in-part of application No. PCT/US2008/056309, filed on Mar. 7, 2008.

(60) Provisional application No. 60/893,574, filed on Mar. 7, 2007, provisional application No. 61/051,979, filed on May 9, 2008.

(51) Int. Cl.
*G09G 5/00* (2006.01)

(52) U.S. Cl.
USPC .......................... 345/7; 351/159.02; 250/221

(58) Field of Classification Search
USPC ............................ 348/739; 345/158; 351/219
See application file for complete search history.

(56) References Cited

U.S. PATENT DOCUMENTS

| | | | | | |
|---|---|---|---|---|---|
| 3,589,800 | A | * | 6/1971 | Cardona | 351/221 |
| 3,630,602 | A | * | 12/1971 | Herbert | 351/221 |
| 3,944,341 | A | * | 3/1976 | Pomerantzeff | 351/206 |
| 3,954,329 | A | * | 5/1976 | Pomerantzeff | 351/221 |
| 4,007,980 | A | * | 2/1977 | Bracher et al. | 351/219 |
| 4,169,664 | A | * | 10/1979 | Bailey, Jr. | 351/226 |
| 4,485,820 | A | * | 12/1984 | Flower | 600/320 |
| 4,553,824 | A | * | 11/1985 | Abe | 351/219 |
| 4,871,247 | A | * | 10/1989 | Haynes | 351/219 |
| 5,024,518 | A | * | 6/1991 | Richards et al. | 351/219 |
| 5,359,372 | A | * | 10/1994 | Kida et al. | 351/219 |
| 5,682,210 | A | * | 10/1997 | Weirich | 348/739 |
| 6,221,028 | B1 | * | 4/2001 | Lieberman et al. | 600/558 |
| 6,396,497 | B1 | * | 5/2002 | Reichlen | 345/427 |
| 6,681,127 | B2 | * | 1/2004 | March | 600/319 |
| 7,202,852 | B2 | * | 4/2007 | Harvie | 345/158 |
| 7,931,832 | B2 | * | 4/2011 | Pugh et al. | 264/1.32 |

(Continued)

FOREIGN PATENT DOCUMENTS

JP 2003279904 A * 10/2003
JP 2005311823 A * 11/2005

*Primary Examiner* — Alexander Eisen
*Assistant Examiner* — Sanjiv D Patel
(74) *Attorney, Agent, or Firm* — Christensen O'Connor Johnson Kindness PLLC

(57) ABSTRACT

A light-emitting contact lens and a method and system for tracking a user's eye position using the light-emitting contact lens are disclosed. The eye position tracking can be used, for example, to allow the user to interact with a display device such that the position of the user's eye determines the image generated by the display device. Thus, as the user's eye moves, the image on the display device will be altered to represent the new position (e.g., viewing angle) of the user with regard to the display device.

17 Claims, 7 Drawing Sheets

U.S. PATENT DOCUMENTS

| | | | | |
|---|---|---|---|---|
| 8,096,654 B2 * | 1/2012 | Amirparviz et al. | ....... | 351/159.4 |
| 2006/0227067 A1 * | 10/2006 | Iwasaki | ............................ | 345/8 |
| 2006/0267768 A1 * | 11/2006 | Sabeta | ....................... | 340/572.1 |
| 2007/0016074 A1 * | 1/2007 | Abreu | ........................... | 600/475 |
| 2008/0024597 A1 * | 1/2008 | Yang et al. | ...................... | 348/53 |

* cited by examiner

CONTACT LENS WITH INTEGRATED LIGHT-EMITTING COMPONENT

CROSS-REFERENCES TO RELATED APPLICATIONS

This application is a continuation-in-part of International Application No. PCT/US2008/056309, filed Mar. 7, 2008, which claims the benefit of U.S. Provisional Application No. 60/893,574, filed Mar. 7, 2007. This application also claims the benefit of U.S. Provisional Application No. 61/051,979, filed May 9, 2008. Each application is incorporated herein by reference in its entirety.

BACKGROUND

Recent advances in methods for fabricating micro-scale electronic components, and in methods for self-assembly of micro-scale components onto separately-formed substrates, are enabling the fabrication of systems that were previously impossible or impractical to construct. For example, the ability to incorporate silicon-based components onto polymeric substrates to form functional devices provides new opportunities and challenges for producing useful systems.

The advantages of systems for reliably displaying information to users in a manner that minimizes the user's need to look towards a fixed display device are well-known. For example, heads-up displays have been built into aircraft cockpit windows and military headgear. For commercial applications, wearable display devices such as head-mounted displays or devices that project images directly onto a user's retina have been developed.

It is also useful in some applications to be able to monitor an individual's biological condition, for example to evaluate chemical or biological stressors that may be present internally or externally, to monitor an individual's level of exertion, or to evaluate potential traumatic stressors, or the like. Various biosensors are, of course, known in the art, but there remains a need for providing a system for reliably collecting and monitoring biological information produced by such biosensors.

Improvements in systems for displaying information to a user, and improvements in systems capable of sensing and/or monitoring biological attributes of a user would fill such needs.

Furthermore, as video gaming technology increases in complexity, it has become desirable to ascertain the position of a user's body parts (e.g., limbs, head) as the user participates in the game so as to translate the user's body movements into game-controlling functions. The position of a hand-held controller can be determined using lights embedded in the controller that are sensed by a detector interfaced with the video game console. It has been demonstrated that similar lights can be affixed to a user's head to determine head position. There is not currently a technology that uses light to track eye position due the complexity of determining actual eye position (as opposed to simple head position) at a distance.

SUMMARY

In one aspect, a light-emitting contact lens is provided, comprising a transparent substrate shaped to be worn directly over a user's eye having a light-emitting component disposed thereon oriented such that light emitted from the light-emitting component is directed away from the user's eye; and a means for supplying power to the light-emitting component.

In another aspect, a system for tracking eye position is provided, comprising a transparent substrate shaped to be worn directly over a user's eye having a light-emitting component disposed thereon oriented such that light emitted from the light-emitting component is directed away from the user's eye; a means for supplying power to the light-emitting component; and a means for detecting the light emitted from the light-emitting component.

In another aspect, a method for determining eye position is provided, comprising providing a first light-emitting contact lens having a first light-emitting component disposed thereon and oriented such that light emitted from the light-emitting component is directed away from a user's first eye; detecting the light emitted from the first light-emitting component; and using the detected light to determine the position of the first light-emitting component.

In another aspect, a method for generating an image on a display device in relation to the spatial position of a viewer in relation to the display device is provided, comprising determining a first position of a user's first eye through the steps of providing a transparent substrate to the user shaped to be worn directly over a user's first eye having a first light-emitting component disposed thereon oriented such that light is directed away from the user's first eye; detecting the light emitted from the first light-emitting component; and determining the position of the first light-emitting component. The method additionally includes providing a first image on the display device, wherein the first image content is determined by the first position of the user's first eye; determining a second position of a user's first eye through the steps of: detecting the light emitted from the first light-emitting component; and determining the position of the first light-emitting component; and providing a second image on the display device, wherein the second image content is determined by the second position of the user's first eye.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

An electronically functional contact lens, or active contact lens, and methods for constructing a prototype active contact lens are disclosed.

Briefly describing the embodiments disclosed, an active contact lens is fabricated that includes an active component (e.g., a light-emitting component or biosensor). If the active component requires power, such power can be supplied either on- or off-lens. The active contact lens provides information to the user (e.g., through a light-emitting display), information about the user's body (e.g., through a biosensor), or information about the location of the lens (e.g., through an outwardly directed light-emitting component coupled with a detector that detects emitted light off-lens).

Two currently preferred embodiment of an active contact lens system will be described, with reference to the FIGURES, wherein like numbers indicate like parts. In the first preferred embodiment described below, the active contact lens includes a biosensor and/or a semi-transparent display allowing a user of the lens to view an image on the display.

In the second preferred embodiment, a light-emitting component is integrated into the active contact lens such that the light is emitted away from the user's eye. The light emitted from the lens can optionally be detected and the position of the user's eye determined (e.g., for interfacing with a display device such that the position of the user's eye determines the content of the display).

The preferred embodiments are not intended to be limiting, and additional embodiments are contemplated wherein an active contact lens can be formed integrating any number of active components. For example, an infrared light-detecting component can be integrated into an active contact lens, thus allowing the active contact lens to detect infrared light that cannot be detected by the user's natural eye.

Figure 1:
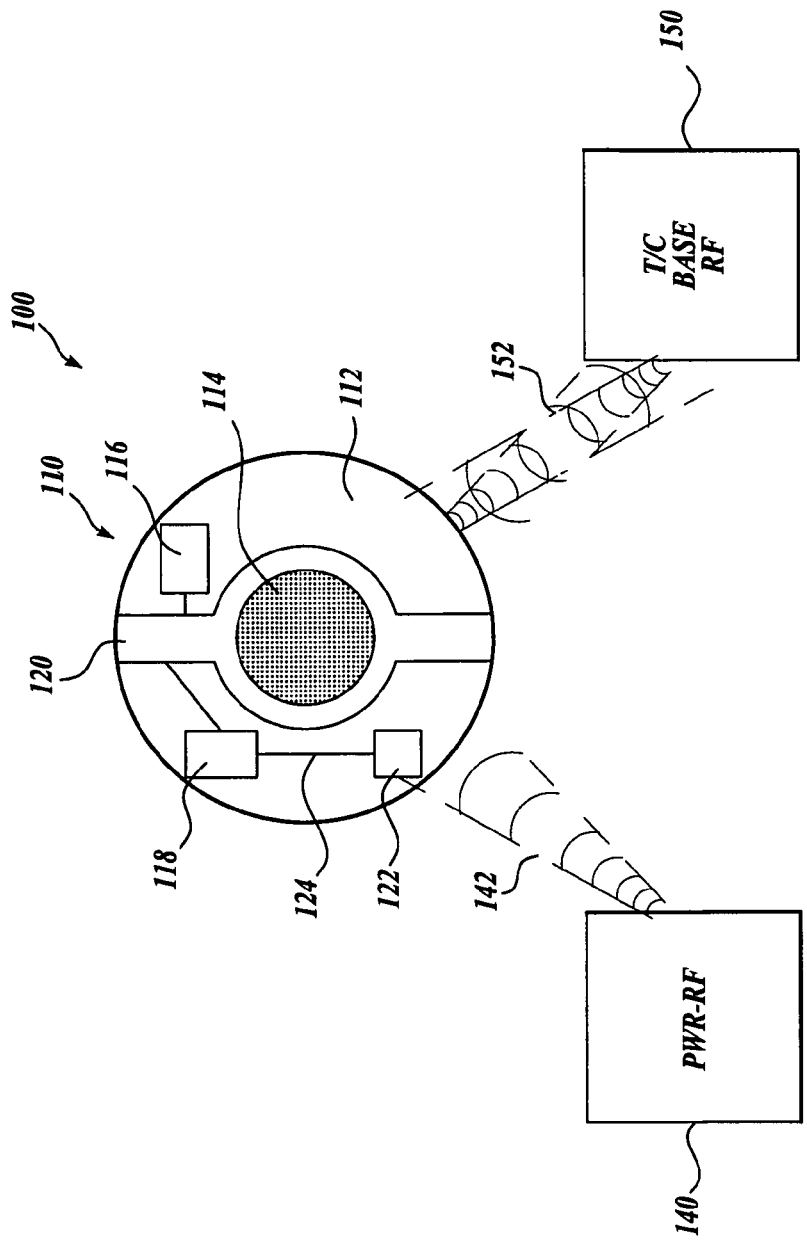
FIG. 1 is a schematic diagram of an active contact lens system in accordance with the present invention.
Figure 2:
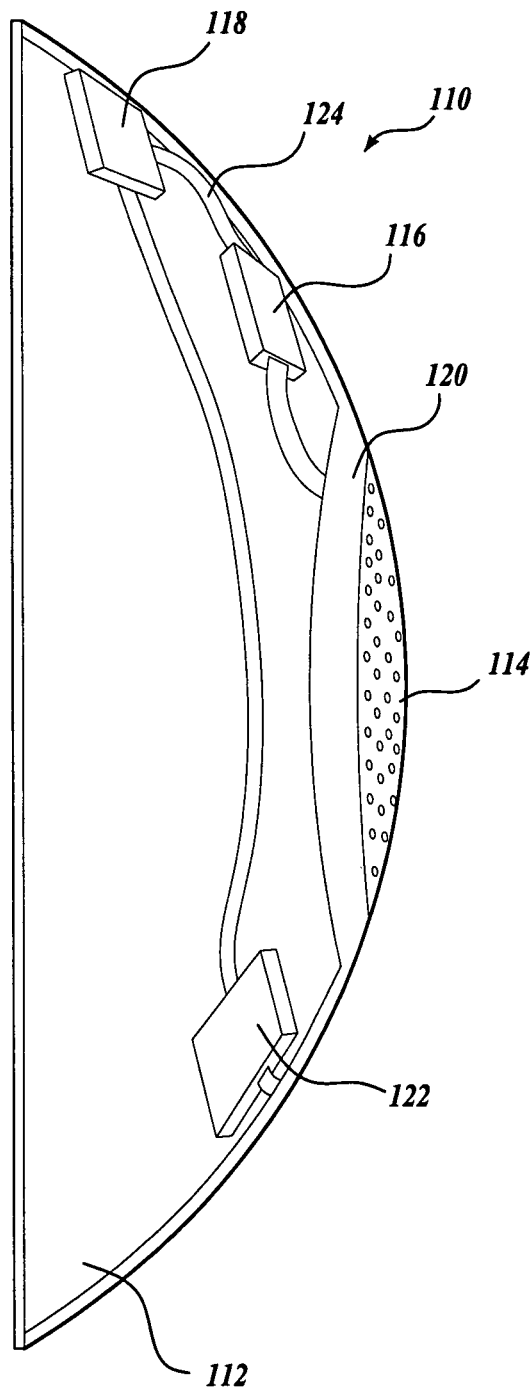
FIG. 2 is a side view of the active contact lens shown in FIG. 1.

Overview of a First Embodiment: Active Contact Lens Having an Integrated Display Device and/or Biosensor FIG. 1 shows schematically an active contact lens system 100 in accordance with the present invention, which includes an active contact lens 110, a power supply 140, and a base station 150. FIG. 2 shows a side view of the active contact lens 110 component of the system 100.

In this embodiment, the active contact lens 110 is formed on a transparent substrate 112, and includes one or more of a semi-transparent display 114, a display drive circuit 116, a data communications circuit 118, an energy transfer antenna 120, a biosensor module 122, and embedded interconnects 124 that functionally connect the various components assembled on the substrate 112. Preferably, the power supply 140 is an RF power supply and the energy transfer antenna 120 is an RF energy transfer antenna adapted to receive power via radio frequency waves 142 for powering the components of the active contact lens 110. Preferably, the base station 150 is an RF ultra-low-power base station adapted to send and receives encrypted data via radio waves 152 to and from the active contact lens 110, as described in more detail below. It is contemplated that the energy transfer antenna 120 may also be utilized for transmitting and/or receiving data for the data communications circuit 118. Alternatively, a separate antenna (not shown) may be provided in the data communications circuit 118 for exchanging data with the active contact lens 110.

In this embodiment the active contact lens system 100 may perform one or both of two classes of functions:

a) The active contact lens 110 may incorporate the semi-transparent display 114 that allows for providing visual information to the user; and/or b) The active contact lens 110 may incorporate one or more biosensors 122, for example to continuously monitor physiological and immunological conditions of the user.

The radio frequency (RF) power supply 140 powers the active contact lens 110 through a base antenna (not shown) which is designed to cooperate with the RF energy transfer antenna 120 positioned on the active contact lens 110 to power the active elements on the lens 110 through the data communications circuit 118. It is contemplated that the power supply 140 may conveniently be worn by the user (for example, attached to a belt, integrated into the user's cloths, etc.) to provide a fully mobile system, and keep the power supply 140 in close proximity to the active contact lens 110.

The RF ultra low-power encrypted telecommunication base station 150, which may be constructed separate from or integral with the power supply 140, exchanges data with the active contact lens 110. It is contemplated that the base station 150 may also be adapted to be worn by the user. The data exchanged between the active contact lens 110 and the base station 150 may include, for example, data to the display drive circuit 116 to refresh pixels in the display 114 to display the desired visual information. Concurrently, the biosensor(s) 122, typically disposed on the surface of the lens 110, may sample and analyze the corneal interstitial fluid, detect heart rate data, or the like. Biomarker measurement results are relayed back to the base station 150, which may be used to assess the user's health condition.

The active contact lens system 100 allows for full situational awareness and mobility by enabling real-time information display to permit quick decision-making. The potential applications in gaming, virtual reality, and training are innumerable, and will be readily apparent to persons of skill in these arts.

The incorporation of biosensor(s) 122 onto the active contact lens 110 allows, for example, continuous sampling of the interstitial fluid on a user's cornea. This fluid is in indirect contact with blood serum via the capillaries in the structure of the eye and contains many of the markers that are used in blood analysis to determine a person's health condition. The sampling and analysis of this fluid allows for continuous assessment of a user's fatigue level and early detection of infectious components without taking a blood sample. The same interstitial fluid can be used to assess the user's blood glucose level allowing for continuous glucose monitoring without blood sampling for diabetic patients.

Certain aspects and design goals of a preferred embodiment of the active contact lens system 100 will now be discussed, to aid the reader in understanding the present invention. In a preferred embodiment, all of the RF and display driver circuitry are conveniently deployed in silicon. Although it is difficult in the prior art to combine silicon-based components with plastic substrates, the present inventor has recently demonstrated it is possible to incorporate free-standing microfabricated silicon circuit components on plastic substrates using fluidic self-assembly techniques. Fluidic self-assembly may be used to integrate independently fabricated silicon circuit elements into the structure of the contact lens substrate.

Temperature Considerations

It is important to minimize the power consumption of the display drive circuit 116, the data communications circuit 118 and related electronics in order to keep peak temperature of the active contact lens 110 low. For humans, the central cornea typically has a temperature of about 34° C., with an increase of around 0.50° C. at the edges of the eye and in the corneal limbus. This temperature can be affected by contact lens wear, which can lead to changes in epithelial metabolic activity. Changes in metabolic activity can lead to changes in oxygen consumption of the corneal cells, which can in turn alter the balance of oxygen consumption and corneal demands. Larger increases in temperature can result in corneal hyperthermia and cell damage. Long-term damage can result in the form of cataracts. It has been reported that the temperature threshold for radio-frequency induced corneal damage is 41 to 55° C.

In one embodiment of the active contact lens 110, a poly methyl methacrylate ("PMMA") substrate 112 was selected. In general, the substrate material from which a contact lens is constructed must be compatible with the ocular environment, chemically stable, optically clear, have an appropriate refractive index, and have a low contact angle with the tear film so that it is 'wetted' by the eye. PMMA, an acrylic resin, was early identified as a potential contact lens material to meet these specifications. Impermeable hard contact lenses consisting of PMMA were the first type of contact lens to gain wide use among the public. Because of their low weight, ability to be manufactured into very thin lenses, and high optical quality, PMMA based contact lenses were the standard for contact lenses world wide from the 1930's through the late 1970's.

PMMA is relatively non-reactive with biological tissues. Protein adsorption on the lens surface is minimal, and the lenses are easily disinfected of bacteria. However conventional PMMA lenses have low oxygen permeability. The cornea is an avascular tissue, which obtains its nutrients and oxygen supply directly from the environment and corneal fluids such as the tear fluid. Studies suggest that PMMA lenses can reduce the mitotic rate of epithelial cells, thus decreasing the cornea's ability to repair damage and respond to stress. Therefore, PMMA lenses are recommended for daily use of around eight hours or less.

Although PMMA are currently only used in a limited capacity for contact lenses, it is nevertheless a good choice as a prototype material for use as the substrate 112 for active contact lenses 110. Reasons for the use of PMMA as a prototype material include: well documented and tested material interactions with the ocular environment, mechanical reliability, and ease of manufacturing. It is contemplated that other materials such as rigid gas permeable lenses ("RGPs") may alternatively be used for the substrate 112. A major difference between the RGP contact lens materials and PMMA is oxygen permeability. RGP is specifically engineered to allow more oxygen to reach the corneal surface. However, because PMMA has been demonstrated to be a safe contact lens (for limited daily use), it is a strong choice as a prototype material. Using the proper microfabrication procedure, it is possible to make a porous PMMA contact lens and at least partially alleviate the oxygen impermeability of the polymer.

A straightforward calculation can be done to estimate temperature effects for an exemplary contact lens system 100. Of course, heat dissipated by the active contact lens 110 will increase the temperature of the corneal surface. Assuming 150 mW power dissipation in the active contact lens 110. Assume also the thermal conductivity of the PMMA substrate is about $K_{PMMA}=0.25$ mW/mm-° K and the thermal conductivity of the cornea is about $K_{Cornea}=0.58$ mW/mm-° K. With these assumptions, the temperature change at the surface of the cornea is 1.6° C.

Therefore, the total temperature at the surface of the cornea is around 35.6° C. with the active contact lens 110 at the corneal surface. This is much below the threshold of 41° C. for corneal damage. In addition, in a similar temperature simulation dealing with intraocular implants it was found that the worst-case scenario with 46 mW of heat dissipation is that there is a peak temperature increase of 0.75° C. Therefore, the total power generation of the active contact lens 110 is unlikely to lead to a temperature increase that will damage the cornea.

Image Display

The active contact lens 110 places the display 114 light sources, for example LEDs, substantially on the surface of the cornea. A person cannot focus on objects that are closer than a few centimeters. At least two illustrative approaches are available for generating a sharp image on a user's retina from light generated by the display 114: i) assembling or fabricating microlenses (not shown) under each pixel of the display 114 to form a collimated beam that may be projected to the retina such that the beam is interpreted as a far-field source; or ii) forming artificial images by determining the proper pixel switching algorithms using conventional imaging transformations.

Power Subsystem

The RF power transmission subsystem comprises the power supply 140 and the receiving energy transfer antenna 120. It is contemplated that the power supply 140 may conveniently be formed to be worn by the user. The antenna 120 may be made with high dielectric constant insulators to reduce size, and may be adapted for operation in the 1.2-5 GHz frequency range, for example. Rectenna structures, that combine nonlinear devices with standard linear antennas, form the basis of RF power reception. For example, a high frequency patch antenna may be constructed as an annular or loop-shaped element that surrounds the middle section of the lens, leaving the middle section transparent for formation of the semi-transparent display 114.

Biosensors

Biosensors 122 may be fabricated independently and self-assembled onto the substrate 112. A candidate transduction mechanism for the biosensors 122 is based on functionalized silicon nanostructures that change conductivity as a result of binding to a specific target molecule. Such nanoscale biosensors 122 can be used for direct electrical detection of ions, DNA and proteins. Multifunctional sensors for measurement of soluble factor concentrations and viscosity may also be provided on the active contact lens 110. The biosensors 122 may also be provided and monitored, for example to provide early detection of pathogens or external sources of irritation in the tear film/fluid.

Applications

It is contemplated that the active contact lens system 100 will have a multitude of application, including applications wherein confidential information display is desired, or wherein the display of information that does not require a user to look away from a particular field of view (so-called heads-up displays). The system 100 may also be used for virtual reality training and/or for gaming applications.

The active contact lens system 100 may also allow for continuous monitoring of the physiological conditions of a user without blood sampling. This information can be recorded and relayed to a central location to determine the general level of health. In case of injury, the contact lens can make vital marker levels available before taking a blood sample and the following analysis is possible.

The system is also believed to have potential use for entertainment (gaming) and health-care (sampling of the tear film glucose level and its correlation to systemic glucose abnormalities). It is contemplated that visible and infrared cameras, adaptive tele-lenses, high-resolution color displays, and more complex biosensors may be integrated into the system. For example, light detecting components may be utilized to generally capture and transmit images of what the user sees.

The currently preferred active contact lens 110 is a multi-functional chip integrating electronic, radio frequency, photonic, electro-optic, and bio-sensing components on a three-dimensional (3D) polymer platform 112. The following sections discuss the technical approach taken to design and construct various sub-systems of the active contact lens 110 including the display 114, RF power supply 140, and biosensors 122; and to use self-assembly to integrate the whole system.

Prototype Construction

Details relating to the construction of a prototype active contact lens system 100 will now be provided as an aid to understanding the present invention.

The basic platform of the prototype active contact lens 110 is constructed on a nominally 100 μm thin biocompatible polymer substrate 112. The microfabrication steps used to incorporate the display pixel structures for the semi-transparent display 114, the embedded metal interconnects 124, and the binding sites for silicon chips associated with the display drive circuit 116, data communications circuit 118, biosensor module 122 and antenna 120 are performed on the transparent substrate 112 in planar form. After assembly and encapsulation of the active components under a second polymer thin film, the substrate 112 is micro-molded into the desired 3D lens shape to finish the active contact lens 110.

The current preferred method for construction of the display 114 is accomplished using fluidic self-assembly. In this method, the substrate 112 is first provided with the embedded interconnects 124 and binding sites (not shown) with known geometry to guide the self-assembly process. The binding sites on the plastic substrate 112 are formed as recesses that are specifically shaped to accommodate a particular component, and then free-standing microfabricated components are passed over the substrate 112 in a fluid environment such that the components self-assemble into desired positions. Using this technique the present inventors have successfully demonstrated high yield assembly of functional devices. A suitable self-assembly methodology is disclosed in U.S. provisional patent application Nos. 60/816,217 and 60/883,696, which are hereby incorporated by reference in their entirety.

A fluidic self-assembly method is preferred to fabricate the semi-transparent display 114 on the contact lens substrate 112. Of course, the semi-transparent display 114 may be fabricated with opaque elements spaced apart on the transparent substrate, producing a semi-transparency for the assembly as a whole. Micron-scale light-emitting diodes ("LEDs") can be fabricated in compound semiconductor substrates (AlxGa1-xAs), and released to produce free-standing LEDs, and then re-assembled on the substrate 112 to form the semi-transparent display 114. Alternatively, organic semiconductors are available and may be used to form the display in applications where organic LEDs are beneficial.

Figure 3:
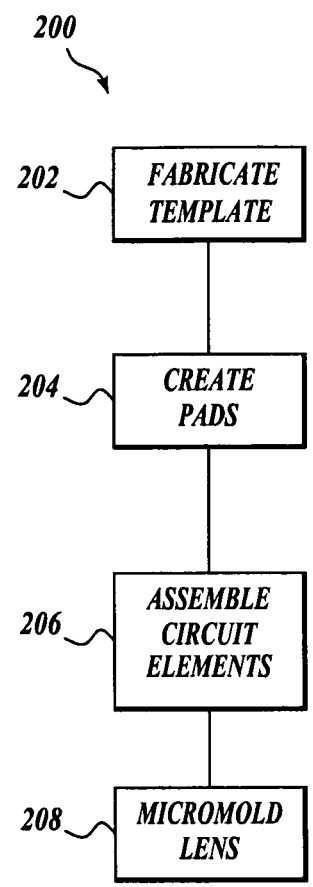
FIG. 3 is a flow chart showing a method for fabricating an active contact lens such as the active contact lens shown in FIG. 1.

A current fabrication method 200 for the prototype display 114 involves four major steps, as shown in FIG. 3. The first step is template fabrication 202 to pattern a substrate so that it may act as a template onto which circuit elements can be assembled. The second step is to create solder alloy compatible pads 204 for the circuit elements. The third step involves assembling circuit elements 206 onto the template and heating the system in order for the alloy to create an electrical connection between the circuit elements and the template interconnects. The final step is to micro-mold the template 208 into a contact lens shape.

1. Template Fabrication

The template fabrication can be broken down into six steps, four of which involve depositing layers of material using standard photolithography and/or lift-off. The fifth step is to cut the templates into 1.6 mm diameter discs. The last step is to dip the template into an alloy bath to deposit the alloy for creating electrical connection between the template interconnects and the assembled circuit elements.

The prototype active contact lens 110 was fabricated on a 100 mm polyethylene terephthalate ("PET") wafer. The wafer is first sprayed with acetone and isopropanol ("IPA") prior to patterning. Nitrogen gas is blown across the wafer in order to dry the wafer and remove any particulates.

The wafer is then loaded into a spincoater where P20 adhesion promoter is deposited followed by AZ4620 positive photoresist. The wafer is spun with a spread speed of 500 rpm and a spin speed of 5000 rpm with a ramp up rate of 100 rpm/s and 1000 rpm/s respectively. The resulting film is approximately 5 microns in thickness.

The wafer is then placed onto a 35° C. hotplate and the temperature is ramped up to 65° C. at a rate of 2° C. per minute. The wafer is then baked at 65° C. for 5 minutes before the temperature is ramped back down to 35° C. at 2° C. per minute.

The wafer is then loaded into a UV exposure/aligner system where the photoresist can be patterned using a photomask and UV exposure. The photoresist is exposed to both 405 nm and 365 nm UV light at an intensity of 13 mJ/cm$^2$ for 40 seconds. The wafer is placed into a 400K developer bath for 1 minute and is then is transferred to a de-ionized (DI) water bath for rinsing. After rinsing, the wafer is dried using nitrogen gas. The wafer is then placed in 100-Watt plasma for 10 minutes at 1 Torr oxygen to clean the surface.

Next, the wafer is placed into an electron beam evaporation chamber where approximately 5 nm of chrome, 150 nm of nickel, and 100 nm of gold is deposited. The wafer is then placed into a bath of acetone for 1 hour and then ultra-sonicated for 10 seconds. The lift-off completed with an acetone and IPA rinse followed by a N$_2$ drying. At this point the first layer of metal interconnect is patterned.

The second layer is an SU8 insulating layer that allows wires on the template to cross. The wafer is placed in 100 W plasma for 2 minutes at 1 Torr oxygen. The negative photoresist SU8-2 is spun onto the wafer at a spread speed of 500 rpm and speed of 4000 rpm, with ramp speeds of 100 rpm/s and 500 rpm/s respectively.

The wafer is placed on to a 35° C. hotplate for soft-bake and is ramped up to 65° C. at 2° C. per minute. The wafer is held at 65° C. for 5 minutes then temperature is ramped back down to 35° C. The SU8 is patterned with both 405 nm and 365 nm UV light at an intensity of 13 mJ/cm$^2$ for 15 seconds. The same baking steps are then applied again as previously described. The wafer is then placed in a SU8 developer bath for 1 minute, rinsed with IPA, and blown dry with N$_2$. This completes 2 layers of the template.

The third layer is a metal layer that is deposited on top of the SU8-2 insulating bridges. Generally, the same method that is used to define the first layer is used here to define the third layer, and the like steps are not repeated for brevity. There are, however, two differences: the metallization is done through sputtering instead of electron beam evaporation and the lift-off is done over a period of 12 hours. The metals sputtered are 5 nm of titanium tungsten alloy and 300 nm of gold. The lift-off process is changed so that the wafer soaks in an acetone bath for 12 hours and is not sonicated.

The final layer acts to encapsulate the surface in a thick SU8 layer so that regions for circuit assembly can be clearly defined. The wafer is again plasma cleaned at 100 Watts in 1 Torr oxygen for 2 minutes. The resist used is now a thicker SU8-5 which is spun with a spread speed of 500 rpm and a speed of 3000 rpm with ramp speeds of 100 rpm/s and 500 rpm/s respectively.

The wafer is placed on a hotplate for soft-bake at 35° C. and is ramped to 65° C. at 2° C./min. The temperature is held at 65° C. for 5 minutes before it is ramped up to 95° C. at 2°

C./min. The wafer is held at 95° C. for 5 minutes and then the temperature is ramped down to 35° C. at 2° C./min. The thicker SU8 is patterned with both 405 nm and 365 nm UV light at an intensity of 13 mJ/cm$^2$ for 20 seconds. The wafer is then baked again with the same soft-bake recipe, heating the wafer up to 95° C. The wafer is placed into a SU8 developer bath for 2 minutes, rinsed with IPA, and blown dry with $N_2$.

The wafer is then cut with a $CO_2$ laser for the desired contact lens element. The backside of the wafer is bonded to dicing tape and the wafer is taped into a cutting stage. The stage is then sealed and $CO_2$ gas is introduced into the stage. A computer program guides the laser cutter and cuts out each individual contact lens blank.

Each individual contact lens blank is peeled off the dicing tape and is cleaned with an IPA rinse and $N_2$ blow drying. The contact lens blank is then placed in to a sonicating molten alloy bath at 70° C. for 5 seconds. The alloy will deposit on any exposed metal surface that is no encapsulated by the fourth SU8 layer. This alloy bumping will allow the circuit elements to bond to the template.

2. Creating Alloy Compatible Pads

The alloy used on the template will not wet the aluminum bonding pads that are typically found on VLSI chips. Thus it is necessary to create the proper metal system on the bonding pads so that the alloy will wet both the template and circuit chip.

The first step is to remove any aluminum oxide that has built up on the pad. The chips are soaked in 5% sodium hydroxide solution by mass for 10 seconds, rinsed with DI water, soaked in 50% nitric acid by volume for 10 seconds, and rinsed with DI water before being placed in a zincate bath for 30 seconds. The zincate bath will electrolessly deposit zinc on the aluminum pads.

The first zinc layer is then removed by placing the chip back into the 50% nitric acid bath for 10 seconds followed by DI water rinse. The chip is again immersed in the zincate solution for 1 minute and rinsed with DI water.

The zinc layer will allow the chip to be placed into an electroless nickel bath. The chip is placed into a 90° C. nickel bath for 1 minute and is rinsed with DI water. The nickel layer now allows the chip to be placed into a 75° C. gold electroless bath for 5 minutes. The chip is then rinsed with DI water and is blown dry with $N_2$. The resulting gold film will be approximately 200 nm in thickness.

3. Circuit Element Assembly

The template and circuit elements are now assembled manually or with self-assembly. The larger integrated circuits can be assembled manually, while the LED elements are assembled using self-assembly. The bare die integrated circuits are flip-chipped onto the template regions defined by the thick SU8 layer. The entire system is then heated up to approximately 70° C. which causes the alloy to melt and create an electrical connection between the template interconnects and the circuit elements.

4. Micromolding

The contact is now placed into an aluminum mold that is heated to approximately 95-100° C. The two halves of the mold are pressed down with the contact in between them. The heat causes the PET to be malleable and thus the contact conforms to the shape of a contact lens. The mold and contact are allowed to cool. The contact is removed, retaining its curvature.

5. 64-LED Display Drive Circuit

Figure 4:
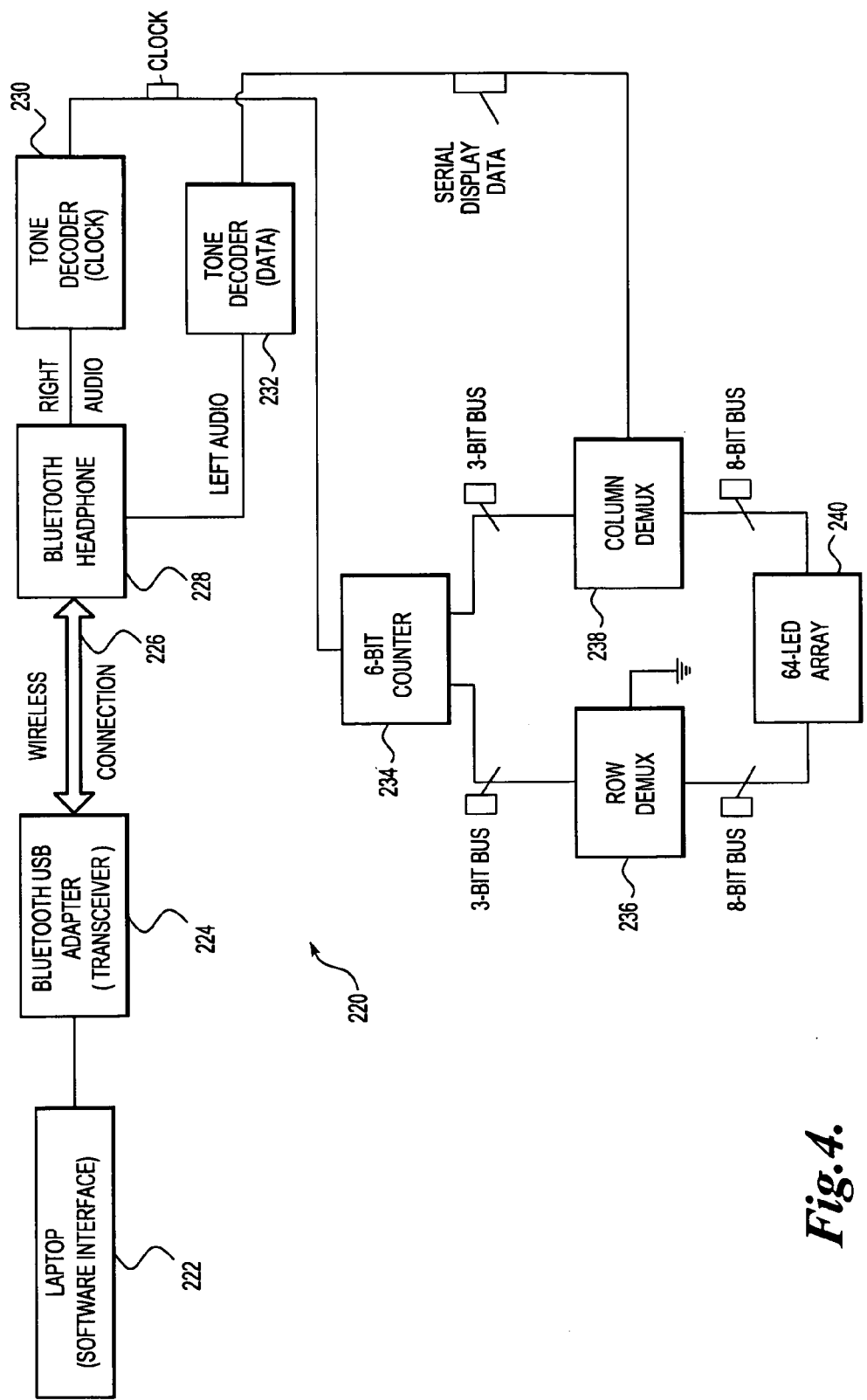
FIG. 4 is a block diagram showing a prototype display drive circuit for an active contact lens such as that shown in FIG. 1.
Figure 5A:
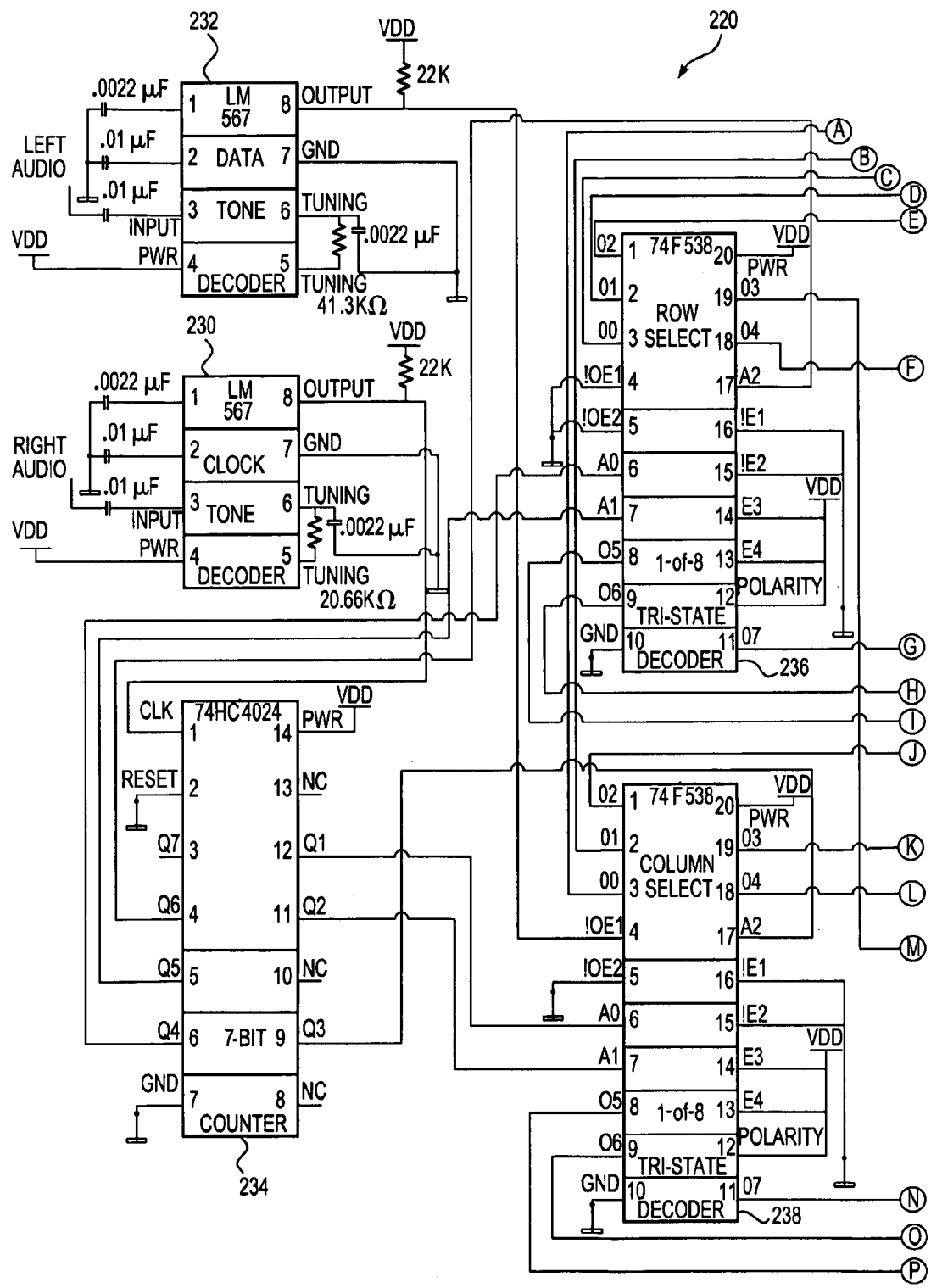
FIGS. 5A and 5B show a schematic diagram of a circuit corresponding to the block diagram of FIG. 4.
Figure 5B:
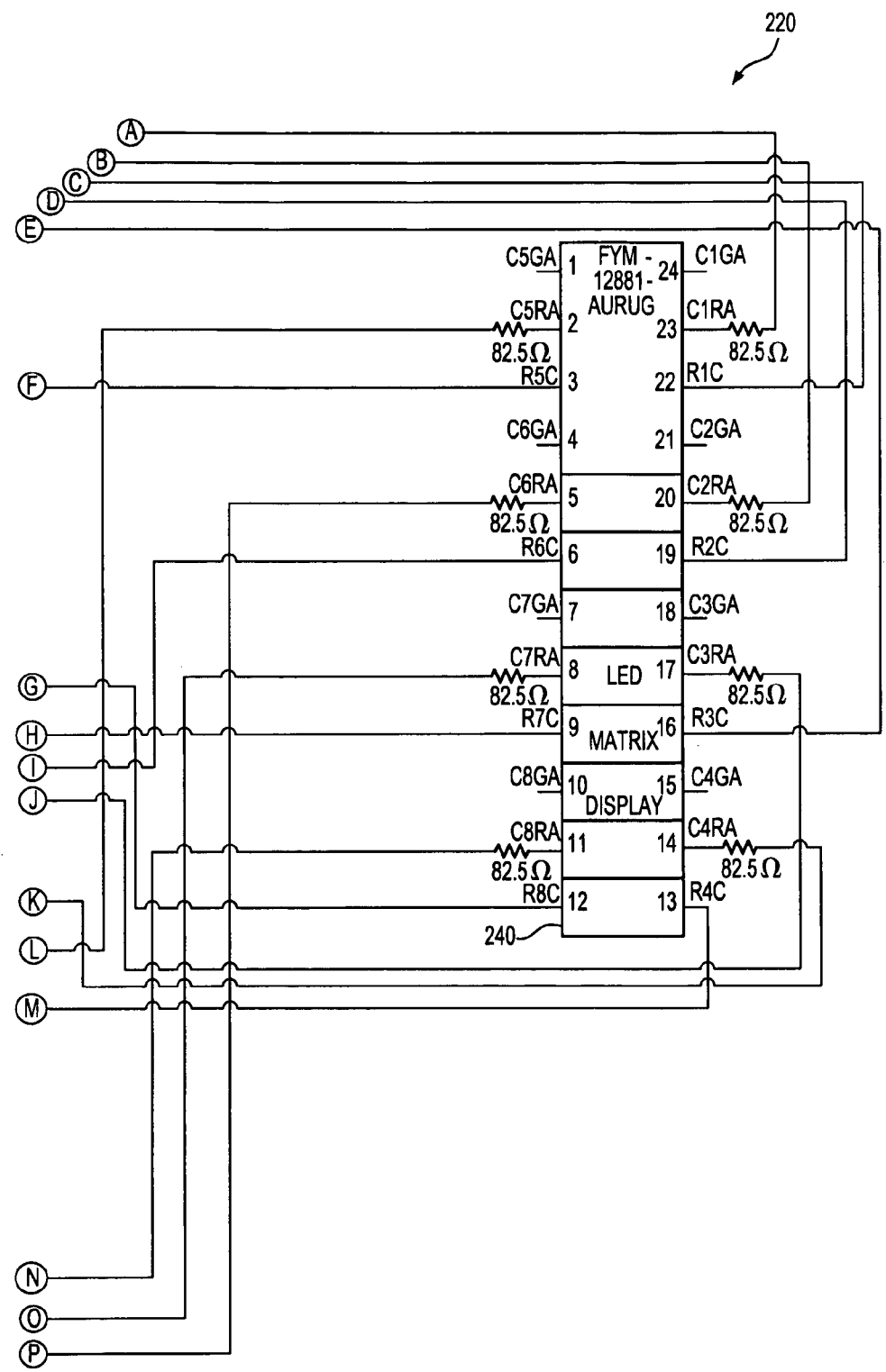

A simple block diagram 220 for operation of an illustrative circuit suitable for the display drive circuit 116 and designed to drive an 8×8 array of LEDs forming the LED display 240 through the use of a bit counter 234 (in the prototype apparatus a 7-bit counter was selected, but only 6 bits were used) and two 3-to-8 bit decoders 230, 232 is shown in FIG. 4. A corresponding illustrative circuit 250 is shown in FIGS. 5A and 5B. In this design the counter 234 is a given clock signal to count from 0 to 63, and the first decoder 230 is given an enable (data) signal to turn on the specific LED that that the counter 234 has counted to.

A CPU 222 such as a laptop with a software interface uses a Bluetooth interface 224 to wirelessly transmit 226 data and clock signals through Bluetooth stereo audio channels to receiver 228. The bits of the data and clock are represented by the presence or absence of a certain audio frequency on each audio channel (left/right). The audio lines from Bluetooth receiver are connected to two audio tone decoder chips 230, 232. If the tone decoder 230, 232 detects the presence of a tone in the correct frequency range, it will pull its output value to a logic zero/low. If the decoder 230, 232 does not detect the correct tone, the output line remains a logic one or high. Using this method it is possible to wirelessly transmit a series of digital bits wirelessly by simply playing audio files on a computer 222 with an attached Bluetooth USB adapter 224. The corresponding counter 234 output is transmitted through row and column demux components 236, 238 to selectively control the LED display 240.

Although the disclosed circuit 250 is believed to be illustrative of an approach to driving a 64-LED display 240, it is contemplated that other circuits and different LED configurations may alternatively be used. In particular, it is contemplated that array of LEDs containing more than 64 LEDs may be used.

The illustrative row and column demux decoders 230, 232 have an 'output disable' input that allows the chip to set the outputs as high impedance rather than logic 1 or 0. The column demux 238 that addresses the columns of the LED display array 240 has the data signal as an input to 'output disable'. The column demux 238 is connected to all the anodes of the LEDs, such that if the data signal is a logic 1 or high, the outputs will go to high impedance. If the data signal is logic 0, the outputs will remain unaffected.

By piecing together a series of tones, continuously on then off, it is possible to create a clock. If the clock is fast enough to count through all 64 LEDs many times a second, the image will appear to be static. It will be appreciated by the artisan that it is therefore possible to select which LEDs turn on, thereby creating an image through the use of an audio file. Of course, it will be appreciated that more conventional LED circuitry may alternatively be used to control the LED display 240

In the current embodiment, circular LED elements were fabricated on a compound semiconductor multilayer structure grown via metal organic chemical vapor deposition (MOCVD). The illustrative free standing LEDs are designed such that they can emit bright red light from both sides, although the metal contacts to the p and n region are both on one side of the LED.

The active LED structure was built on an AlAs layer that acted as a sacrificial layer for the release of the component. Fast etch rate of AlAs in HF (>1.2 µm/min) aided in easy release of the parts from the substrate. The etch rate of the AlGaAs alloys in HF is related to the relative concentration of Al. The etch rate of the ternary alloy, increases slowly with Al concentration, till ~42% Al concentration, after which the etch rate rapidly increases. The alloy concentration in the multilayer is adapted to ensure its integrity during the release step. In addition, two thin GaAs layers were provided at the top and at the bottom of the LED structure for extra protection. The thin 100 nm GaAs layer on bottom of the LEDs is highly p-doped to be conductive for on wafer testing of the devices. The absorption coefficient of GaAs layer at room temperature is ~$2\times10^4$ cm$^{-1}$ for the peak emission wavelength of 689 nm, corresponding to photon energy of 1.8 eV; the thin GaAs layer absorbs about 18 percent of the emitted light.

The active layer is the 100 nm thick Al0.3Ga0.7As layer with a bandgap of 1.8 eV, which has a peak emission wavelength of 689 nm. This active layer is sandwiched between 2 layers with larger bandgaps of 1.92 eV. These layers confine the carriers in active region, allowing the recombination to happen predominantly in this region. The direct bandgap energy of ternary alloys of AlxGa(1-x)As can be calculated through the following equation:

$$E_g = 1.424 + 1.247x (eV) \ (0 < x < 0.42)$$

Where x is the Al concentration. The top 100 nm GaAs layer is almost transparent similar to the bottom one, and is highly n-doped to make low resistance contact to metal pads possible.

In order to make a free standing LED, we fabricate metal contacts onto the LED, and then release the LEDs from the waver such that the LEDs have a desired shape. For example, the LEDs may be formed generally in the shape of circular discs. Unlike conventional designs, both contacts to p-region and n-region are fabricated on one side of each of the LEDs.

As an illustrative example, for the prototype device circular LEDs were fabricated with contacts on one side of each LED by the following steps:

1. Clean and pattern the wafer with AZ4620;
2. Etch through the top three layers using a 15:1 citric acid to hydrogen peroxide wet etch recipe, to access the p-region and removed the photoresist;
3. Pattern another layer of AZ4620 as a mask;
4. Sputter Au/Ni/Au (50 nm/150 nm/150 nm) to make the metal pads; The metal contacts were deposited on the recently exposed center p-region, and the top n-region. The pad on the center p-region was formed as a circle, and the pad on n-region was ring shaped;
5. Patterning a final layer of AZ4620 to define the circular shape of the LEDs.
6. Place the wafer into a 15:1 citric acid to hydrogen peroxide solution, and etch 4.5 um down to the AlAs sacrificial layer; and
7. Release the LEDs in buffered HF which etched the AlAs sacrificial layer. The result is a powder-like collection of microcomponents which were rinsed and collected through a filter with ethanol and stored in isopropanol (IPA).

Making both p-region and n-region contacts on one side of the circular LEDs, enables us to self assemble them on a template with complementary pads in one step.

To realize a fully functional display on plastic, the free-standing LED must be bound to template mechanically and electrically. Fluidic self-assembly is a cost effective and parallel way to accomplish this goal. When the metal pads on LED come into contact with the molten solder alloy, a very strong bond forms between them via capillary forces. Before introducing the elements to the fluidic self-assembly (FSA) bath, the metal pads on LEDs are cleaned so that they will be able to be wetted with the molten solder. The fluid in the vial containing the LEDs were changed with IPA, and then with 0.1N hydrochloric acid. Then the acid was diluted with DI water and replaced by ethylene glycol to be ready for using in self-assembly process. Template to be used for FSA should be solder dipped immediately before the self-assembly, to prevent formation of thick layer of oxide on solder alloy and further contamination of metal pods.

Besides gravity that helps the LEDs to fall into the wells, and minimization of the surface energy of the molten solder, which forms stable electrical and mechanical bond between template and LEDs, fluid flow and external agitation, provided by a shaker, helped the elements to move freely in the fluid. Shape recognition guided the elements to the proper sites on template, and produced good alignment between the pads on LEDs and the template.

The FSA was conducted in heated acidic ethylene glycol at 70° C. The pH was low enough to remove the oxide layer from the solder alloy surface, and not too acidic to degrade the small solder bumps too quickly.

Second Embodiment: Active Contact Lens Having an Outward-Facing Light-Emitting Component While in the first embodiment, described above, the active contact lens optionally included light-emitting components configured to form a display directed at the user's eye, in a second embodiment the light-emitting components are directed outward from the eye, typically as part of a system for determining the position of the user's eye.

Thus, in this embodiment, a light-emitting contact lens and a method and system for tracking eye position using the light-emitting contact lens are disclosed. By tracking a user's eyes instead of simply the user's head, a much greater degree of interaction can be created between the user and a system configured to utilize the eye-tracking information, such as a video game console.

Figure 6:
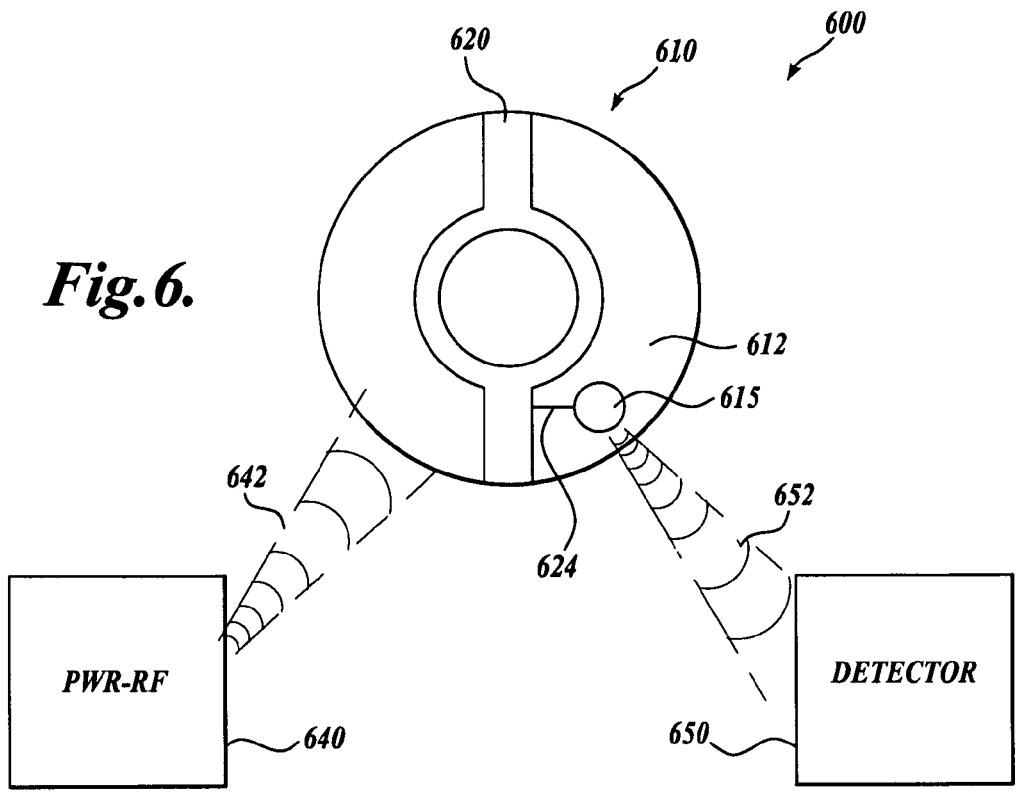
FIG. 6 is a schematic diagram of a light-emitting contact lens in accordance with the present invention.

A current embodiment of the light-emitting contact lens and the system for tracking eye position will be described with reference to FIGS. 6-8. FIG. 6 schematically shows a light-emitting contact lens system 600 for tracking eye position in accordance with the present invention. The system 600 includes a light-emitting contact lens 610 including a transparent substrate 612 and at least one light-emitting component 615 disposed on (or embedded in) the surface of the transparent substrate 612. Power is provided to the light-emitting component 615 by an energy transfer antenna 620 that is in radio frequency (RF) communication with an RF power supply 640 that provides power via radio waves 642.

Figure 7:
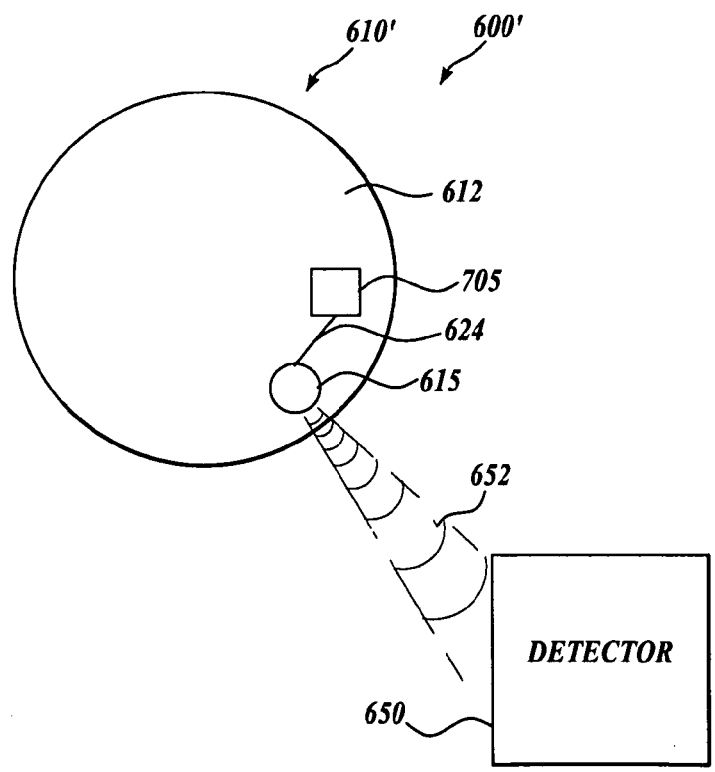
FIG. 7 is a schematic diagram of a light-emitting contact lens in accordance with the present invention.
Figure 8:
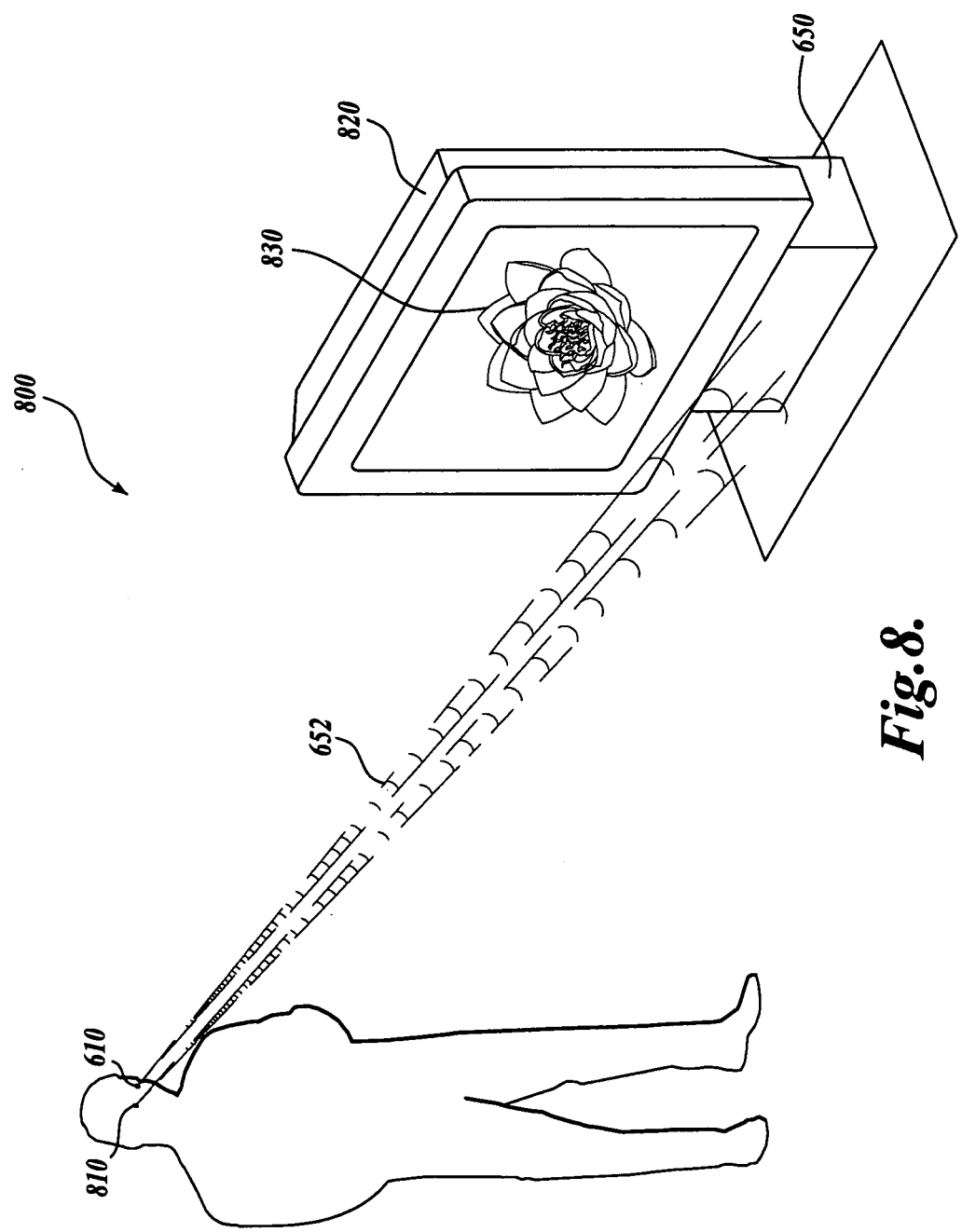
FIG. 8 is a sketch of an eye-tracking image visualization system in accordance with the present invention.

A second embodiment of a light-emitting contact lens system 600' is shown in FIG. 7 where the contact lens 610' has a light-emitting component 615 powered by an entirely on-lens 610' power supply 705 operatively connected to the light-emitting component 615 by an electrical interconnect 624. The on-lens 610' power supply 705 can be any electrical power supply capable of providing enough power to operate the light-emitting component 615. Representative on-chip power supplies 705 include a solar cell, an inertial power-harvesting unit, and a battery. Inertial power harvesting units include traditional meso-scale harvesting units and also MEMS harvesting units, such as those described in Miao et al., "MEMS Inertial Power Generators for Biomedical Applications," *Microsyst. Technol.* 12:1079, 2006, incorporated herein by reference in its entirety.

Representative light-emitting components 615 include light-emitting diodes (LED), micro-lamps, and lasers. The fabrication of typical micro-lamps is described in U.S. Pat. No. 6,650,455, incorporated herein by reference in its entirety. Representative lasers include diode lasers (e.g., edge-emitting diode lasers) and vertical-cavity, surface-emitting lasers (VCSEL).

The systems 600, 600' include a detector 650 for detecting the position of the light-emitting component 615 with respect to distance away from the detector 650 and vertical and horizontal positioning (e.g., using Cartesian or spherical coordinate systems). In a preferred embodiment of a system and method for tracking eye position, as shown in FIGS. 6 and 7, the light-emitting component 615 emits light 652 that is detected by the detector 650. It will be appreciated that the embodiment shown in FIG. 6, powered by a separate RF power supply 640, can include a detector 650 that is combined in a single housing with the RF power supply 640. The distance of the contact lens 610 or 610' from the detector 650 can be determined either by measuring the strength of emitted light from the contact lens and comparing it with a reference signal or, when the user is wearing a light-emitting contact lens 610 or 610' in each eye, by determining an apparent separation of the light sources from each other and using the apparent separation to calculate the distance from the detector 650.

The light-emitting contact lens 610, 610' may additionally include on-lens circuitry (not shown) for controllably modulating the light-emitting component 615. Control of the light-emitting components may be provided exclusively on the substrate 612 or may come from an external wireless link (e.g., a radio-frequency controller that can optionally be integrated with the RF power supply 640 and/or the detector 650).

Three-Dimensional Virtual Display. A currently preferred embodiment of a system and method for tracking eye position using the light-emitting contact lens 610 previously described will now be described further with reference to FIG. 8. A light-emitting contact lens 610 is useful in a system 800 that incorporates the detector 650 to track the position of a user's eye(s) in three-dimensional space via the light-emitting component 615 (FIG. 6) on the contact lens 610. The system 800 provides the means for creating a virtual three-dimensional image 830 on a conventional display device 820. By tracking the eye(s) of a user, the direction that the user is looking can be determined by the system 800 and that positioning data can be used to alter or generate an image 830 on the display device 820 that changes with the changing eye position of the user. Changing user eye position in turn changes the light-emitting contact lens 610 position with respect to the detector 650 and the display device 820. The information displayed 830 (e.g., image) on the display device 820 can be made interactive with the positional data generated by the detector 650, and the image displayed 830 on the display device 820 can be changed in relation to the changing position of the user's eye.

The system 800 described above is useful for several applications. In a first application, the light-emitting components 615 on the contact lens 610 can be used to determine the direction that the user's eye is looking. This information can be used to adaptively and dynamically change the image displayed 830 on the display device 820. For example, only the area of the display device 820 that is being looked at may be kept lit.

In another application of the system 800, a virtual three-dimensional image can be generated. In this application, the display device 820 is perceived by the user as more of a window into another room as opposed to a statically positioned image. In this exemplary embodiment, as the user wearing the contact lens 610 moves closer to the display device 820 the image would change based on the detected position of the user, such that she would be able to see a larger amount of the image displayed 830 on the display device 820 due to a larger perceived viewing angle. Also, when moving, for example, to the left side of the display device 820, more of the right side of the image displayed 830 on the display device 820 becomes visible, and vice versa when moving to the right side of the display device 820. The system 800 can also be used to render three-dimensional the two-dimensional images on the display device 820 that have a perceived depth of field in relation to the user. The parallax between objects of difference distances from the user displayed on the display device 820 results in objects that are meant to be closer to the user moving more than objects meant to be further away when the user moves in relation to the display device 820.

The detector 650 is preferably located near the display device 820 such that the position of the user's eye and the light-emitting contact lens 610 are determined as closely as possible in relation to the display device 820 with which the user is interacting.

In one embodiment, the system 800 includes a second light-emitting contact lens 810 and the detector 650 can distinguish the contact lenses 610, 810 in the different eyes of the user. In this embodiment, the light-emitting component in the first contact lens 610 has a detectably different characteristic than the light-emitting component in the second contact lens 810. The different characteristic may be, for example, the frequency of amplitude modulation or the wavelength of the light emitted. By detecting and distinguishing the different characteristic, the system 800 can generate an additional degree of positioning accuracy between the user, the user's eyes, and the detector 650.

In order to create a virtual three-dimensional visualization system, a relationship between the display device 820 and the user is established. In a representative example the system 800 includes an infrared camera as a detector 650 in conjunction with an infrared light-emitting component 615 on the contact lens 610. The distance between the light-emitting component 615 (or components, if a user is wearing two light-emitting contacts) and the detector 650 can be determined using photogrammetric techniques to extrapolate the user's position, depending on the location and distance between the light-emitting component 615 and the detector 650.

Applications for the visualization system 800 described herein include applications in video gaming. Video games could be enabled to appear in three-dimensional space on a traditional display device when using the described system 800. By tracking a user's eye(s) when bobbing, ducking, and strafing, these movements in real life would become significant movements for the gaming user that would affect the perspective of the displayed image 830 of the game being played by the user.

Contact Lens Fabrication. The complexity of integrating light-emitting components into contact lenses has been a barrier for eye-tracking technology. The fabrication of light-emitting contact lenses can be accomplished using the fabrication processes described herein. A representative fabrication process includes self-assembly of freestanding components in a fluid, such as light-emitting components 615 and on-template power sources 705, and can be performed according to techniques known to those of skill in the art. Radio frequency power receivers 620, antenna, and electrical interconnects 624 can be patterned using standard microfabrication processes known to those of skill in the art.

A representative fabrication process for making a light-emitting contact lens 610 includes fabricating the contact lens 610 using PET plastic as a substrate 612. Light-emitting components are self-assembled in a fluid, and interconnects 624 are fabricated using techniques such as photolithography, vapor deposition of metals, and wet and dry etching.

The lens 610 may further include other components, such as the semi-transparent display 114 and/or biosensors 122, as discussed above.

While illustrative embodiments have been illustrated and described, it will be appreciated that various changes can be made therein without departing from the spirit and scope of the invention.

The embodiments of the invention in which an exclusive property or privilege is claimed are defined as follows:

1. A light-emitting contact lens, comprising
   a transparent substrate shaped to be worn directly over a user's eye having a light-emitting component disposed thereon oriented such that light emitted from the light-emitting component is directed away from the user's eye; and
   a means for supplying power to the light-emitting component.

2. The contact lens of claim 1, wherein the light-emitting component is selected from the group consisting of light-emitting diodes, micro-lamps, and lasers.

3. The contact lens of claim 1, wherein the light emitted from the light-emitting component is infrared light.

4. The contact lens of claim 1, wherein the means for supplying power to the light-emitting component is selected from the group consisting of a battery, a solar cell, an inertial power harvester, and an energy transfer antenna.

5. The contact lens of claim 1, further comprising a second component disposed thereon, said component selected from the group consisting of a semi-transparent display, a light-detecting component, and a biosensor.

6. A system for tracking eye position, comprising
   a transparent substrate shaped to be worn directly over a user's eye having a light-emitting component disposed thereon oriented such that light emitted from the light-emitting component is directed away from the user's eye;
   a means for supplying power to the light-emitting component; and
   a means for detecting the light emitted from the light-emitting component.

7. The system of claim 6, wherein the means for detecting the light emitted from the light-emitting component is selected from the group consisting of a photo diode and a photo-multiplier tube.

8. The system of claim 6, further comprising a display device operatively connected to the means for detecting the light emitted from the light-emitting component.

9. A method for determining eye position comprising:
   providing a first light-emitting contact lens having a first light-emitting component disposed thereon and oriented such that light emitted from the light-emitting component is directed away from a user's first eye;
   detecting the light emitted from the first light-emitting component; and
   using the detected light to determine the position of the first light-emitting component.

10. The method of claim 9, further comprising tracking the position of the first light-emitting component by continuously detecting the light emitted from the first light-emitting component.

11. The method of claim 9, further comprising generating an image on a display device, wherein the image changes based on the determined position of the first light-emitting component.

12. The method of claim 9, further comprising generating a virtual three-dimensional image on a display device that continuously simulates three-dimensional imagery using the position of the first light-emitting component.

13. The method of claim 9, further comprising providing a second light-emitting contact lens having a second light-emitting component disposed thereon oriented such that light is directed away from a user's second eye;
   detecting the light emitted from the second light-emitting component; and
   determining the position of the second light-emitting component.

14. The method of claim 13, further comprising tracking the position of the second light-emitting component by continuously detecting the light emitted from the second light-emitting component.

15. The method of claim 13, wherein the light emitted from the first light-emitting component and the second light-emitting component is different with respect to a characteristic selected from the group consisting of wavelength and amplitude modulation frequency.

16. The method of claim 13, further comprising generating a virtual three-dimensional image on a display device that continuously simulates three-dimensional imagery using the positions of the first light-emitting component and second light-emitting component.

17. A method for generating an image on a display device in relation to the spatial position of a viewer in relation to the display device, comprising
   (a) determining a first position of a user's first eye through the steps of:
      (i) providing a transparent substrate to the user shaped to be worn directly over a user's first eye having a first light-emitting component disposed thereon oriented such that light is directed away from the user's first eye;
      (ii) detecting the light emitted from the first light-emitting component; and
      (iii) determining the position of the first light-emitting component;
   (b) providing a first image on the display device, wherein the first image content is determined by the first position of the user's first eye;
   (c) determining a second position of a user's first eye through the steps of:
      (iv) detecting the light emitted from the first light-emitting component; and
      (v) determining the position of the first light-emitting component; and
   (d) providing a second image on the display device, wherein the second image content is determined by the second position of the user's first eye.

* * * * *